United States Patent [19]

West et al.

[11] 4,111,035

[45] Sep. 5, 1978

[54] ENGINE KNOCK SIGNAL GENERATING APPARATUS WITH NOISE CHANNEL INHIBITING FEEDBACK

[75] Inventors: Gene A. West, Kokomo; Glen C. Hamren, Greentown, both of Ind.

[73] Assignee: General Motors Corporation, Detroit, Mich.

[21] Appl. No.: 848,865

[22] Filed: Nov. 7, 1977

[51] Int. Cl.$^2$ .................... G01N 33/22; G01L 23/22
[52] U.S. Cl. .......................................... 73/35
[58] Field of Search ........................................... 73/35

[56] References Cited
U.S. PATENT DOCUMENTS

| 3,822,583 | 7/1974 | Keller et al. | 73/35 |
| 3,950,981 | 4/1976 | Arrigoni et al. | 73/35 |
| 4,012,942 | 3/1977 | Harned | 73/35 |

*Primary Examiner*—James J. Gill
*Attorney, Agent, or Firm*—Robert M. Sigler

[57] ABSTRACT

A vibration sensor mounted on an internal combustion engine characterized by knock-induced vibrations at a characteristic frequency and by other vibrations is tuned to resonate at substantially the characteristic frequency. A bandpass filter tuned to the characteristic frequency is connected to the vibration sensor output; and the output of the filter is provided to one input of a comparator and to average detector circuitry for generating a unidirectional noise reference signal representing noise at the characteristic frequency, which signal is provided to the other input of the comparator. The knock signal, obtained from the output of the comparator and comprising pulses corresponding to knock-induced peaks of amplitude greater than the unidirectional noise reference signal, is fed back through a low-pass filter to the average detector circuitry in sense to oppose increases in the unidirectional noise reference signal during said knock-induced peaks. The connection of the average detector circuitry to the output of the bandpass filter provides adaptability for mistuned sensors; and the negative feedback to the average detector circuitry reduces the distorting effect, amplified by the bandpass filter, of said knock-induced peaks on the unidirectional noise reference signal, which might otherwise distort the output knock signal.

2 Claims, 8 Drawing Figures

PRIOR ART

ENGINE KNOCK SIGNAL GENERATING APPARATUS WITH NOISE CHANNEL INHIBITING FEEDBACK

BACKGROUND OF THE INVENTION

This invention relates to apparatus for minimizing audible knock in an internal combustion engine by retarding spark timing, when necessary, from the normally set spark timing in response to the signal from an engine mounted vibration sensor. The use of such apparatus may allow an increased engine compression ratio, decreased fuel octane or the use of a turbocharger to boost engine output power and fuel economy, since the system responds to knock to keep it at a low level below audibility and far below any level that might cause harm to the engine.

A particularly difficult problem in such apparatus is the separation of vibrations due to knock, especially at a low level, from all the other vibrations present in an operating internal combustion engine and the generation of a signal accurately representing the intensity of those knock-induced vibrations. Various methods and types of apparatus have been proposed in the prior art for generating a suitable knock signal, but none have been found completely satisfactory in real time automotive engine control.

One technique that has been proposed is frequency discrimination, which takes advantage of the fact that knock has been found to produce vibrations at one or more particular characteristic frequencies, at least in a particular type of engine. It has been suggested that the output of an engine mounted vibration sensor be modified by a bandpass filter tuned to the particular characteristic frequency associated with knock in that engine. Unfortunately, however, this technique by itself has not generally proven to be sufficient in detecting the low levels of knock required, since there is usually noise at the characteristic frequency which is not knock related.

Another technique is amplitude discrimination, in which apparatus is provided for generating a unidirectional noise level reference signal from the sensor output and providing this signal and the sensor output signal to the two inputs of a comparator. The unidirectional noise level reference signal thus masks most of the noise in the sensor output signal so that only the peaks in the sensor output signal rising above the reference level, which are assumed to be mostly due to knock vibrations, contribute to the signal. This technique results in an improvement in signal to noise ratio over the frequency discrimination technique.

Since the amplitude discrimination technique, however, does not distinguish between a high amplitude vibration due to knock and one due to some other cause such as valve noise, the combination of frequency and amplitude discrimination techniques appears to be more practical than either technique alone. Such a combination provides for the sensor signal to be applied through a bandpass filter to a comparator which is also provided with a noise level reference.

In knock signal generating apparatus of the type described above, it has been found that some types of engine mounted vibration sensors tend to resonate at one or more particular frequencies and that these sensors can be at least approximately tuned to the characteristic frequency of vibrations due to knock. Thus the output signal of such a sensor would be already partially filtered and would require less electronic filtering before being applied to the comparator apparatus. Unfortunately, due to such factors as manufacturing tolerances and sensor aging characteristics, sensor-to-sensor variations may appear in the sensor tuning which will produce a wide variation in the output signal level of those vibrations at the design-specified characteristic frequency, although the average output signal broadband noise levels of the various sensors may be consistent. Therefore, the knock signal, which may be obtained by comparing the filtered sensor output signal containing knock-induced peaks at the characteristic frequency to a reference derived from the average broadband noise level, may indicate different knock levels for the same engine knock with different vibration sensors or with the same sensor over time.

The consistency of the apparatus for different sensors can be improved by deriving the noise reference signal from the output of the bandpass filter rather than the output of the sensor, so that the noise reference signal represents noise at the characteristic frequency only and not broadband noise. It is apparent that, if a sensor changes from being tuned precisely to the characteristic frequency to being tuned to some other frequency, the noise reference level at the characteristic frequency will change in the same proportion as the knock-induced output peaks at the characteristic frequency; therefore, the apparatus will produce more consistent results from sensors with varying tuned frequencies.

However, when knock is present, the strong peaks of knock-induced vibrations at the characteristic frequency tend to raise the noise reference and thus reduce the apparent amplitude of knock as seen by the comparator. This effect is magnified by the derivation of the DC reference level from the output of the bandpass filter, since noise components at other frequencies are attenuated with respect to suck knock-induced peaks. This effect may become great enough, when the noise reference level is derived from the bandpass filter output, to affect the ability of the system to respond to strong knock and allow knock to reach a level objectionable to the vehicle operator.

SUMMARY OF THE INVENTION

This invention provides knock signal generating apparatus of the type described above in which both a bandpass filter and a comparator are used to provide frequency and amplitude discrimination in separating the knock induced signals from the noise. It provides for the derivation of the noise reference from the output of the bandpass filter so that the system is adaptable to differently tuned sensors. However, it includes a noise channel inhibiting feedback loop which operates, during large knock-induced vibration excursions in the output signal of the bandpass filter, to reduce the affect of such excursions on the noise reference level.

In a preferred embodiment, the knock signal output of the comparator is fed back through a low pass filter to the input of the noise reference generating means in negative feedback. The resulting knock signal output is a more accurate representation of knock intensity, since the effect of knock on the noise channel is reduced, but is also able to accommodate a variety of sensor tuning and mistuning.

Further details and advantages of this invention will be apparent from the accompanying drawings and following description of a preferred embodiment.

DESCRIPTION OF THE PREFERRED EMBODIMENT

Figure 8:
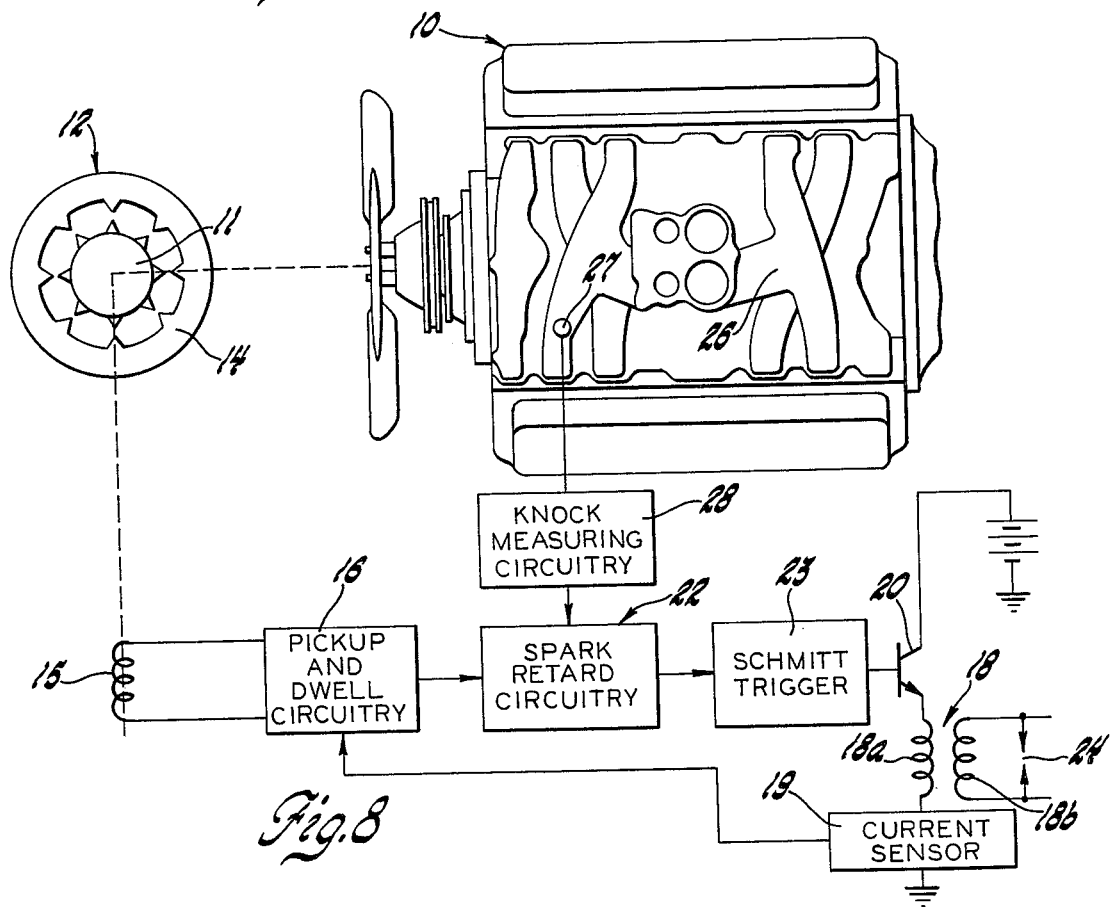
FIG. 8 shows a vehicle-mounted internal combustion engine with an engine-mounted sensor and an ignition spark retard system for use with the apparatus of FIG. 3.

Referring to FIG. 8, an internal combustion engine 10 has a rotating crankshaft which drives the rotor 11 of an alternating current signal generator 12. Generator 12 is a standard spark timing signal generator of the variable reluctance type disclosed and described in U.S. Pat. No. 3,254,247 to Falgy, which issued May 31, 1966. Generator 12 also includes a stator 14 and pickup coil 15 and provides a plurality of equally spaced projections around rotor 11 and stator 14 related to the number of cylinders in engine 10. Relative rotation between the rotor 11 and stator 14 at a speed proportional to engine speed produces a pulsating variation in reluctance which induces an alternating voltage signal in coil 15.

The alternating voltage signal in coil 15 is applied to pickup and dwell circuitry 16, which generates normal spark timing pulses. These normal spark timing pulses could be applied to a Schmitt trigger 23 to control a switching transistor 20 connected to switch current on and off in the primary 18a of a spark coil 18. The flow of current in primary 18a causes electromagnetic energy to build up in spark coil 18; and this energy is released, when transistor 20 cuts off current in primary 18a, in the form of a high voltage spark pulse in coil secondary 18b applied to spark plug 24. A current sensor 19 provides feedback to pickup and dwell circuitry 16 to control the dwell time of current conduction in primary 18a. The system so far described is one well known in the art and shown in the U.S. Pat. No. to Richards et al. 3,828,672, issued Oct. 1, 1974.

In order to selectively retard the spark timing in response to an engine knock signal, spark retard circuitry 22 is inserted between pickup and dwell circuitry 16 and Schmitt trigger 23. Apparatus particularly designed for use with the circuit of FIG. 7 in this application is shown in the U.S. patent application, Ser. No. 789,801, by Gene A. West, filed Apr. 22, 1977 and assigned to the assignee of this application. However, other spark retard circuits are well known in the art.

Engine 10 is provided with an intake manifold 26 on which is mounted, in a position determined by experiment for a particular engine but including the position shown in FIG. 8, a vibration or detonation sensor 27, which may be threaded into a suitably threaded depression provided in manifold 26. Vibration sensor 27 vibrates physically with intake manifold 27 and responds to such vibrations in its axial direction, which is generally normal to the surface of manifold 26 at the position in which it is mounted, to generate an electrical output voltage corresponding to such vibrations. Sensor 27 may be of the type which includes a permanent magnet to generate magnetic flux, an electric pickup coil and a magnetostrictive element within the coil in the path of the magnetic flux to vary the flux with vibration and thus generate the output voltage across the coil. An example of such a vibration sensor is the U.S. patent application, Ser. No. 767,995, by Gerald O. Huntzinger et al., filed Feb. 11, 1977 and assigned to the assignee of this application.

The output signal from vibration 27 is provided to knock measuring circuitry 28 in which a knock intensity signal is generated for application to spark retard circuitry 22 to control the retard of the sparks in spark plug 24 from the normal spark timing. Apparatus for use as knock measuring circuitry 28 is shown in circuit form in FIG. 7 and, with the sensor 27, in block diagram form in FIG. 3.

Figure 1:
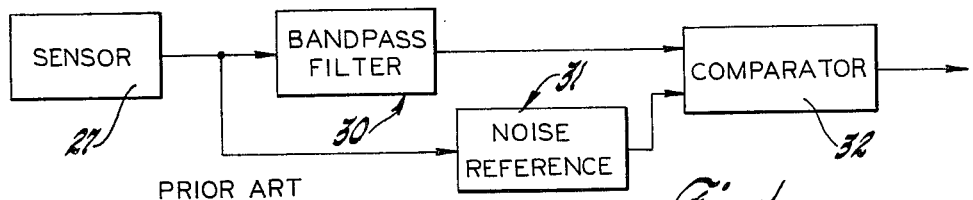
FIG. 1 shows a block diagram of a prior art embodiment of engine knock signal generating apparatus.
Figure 6:
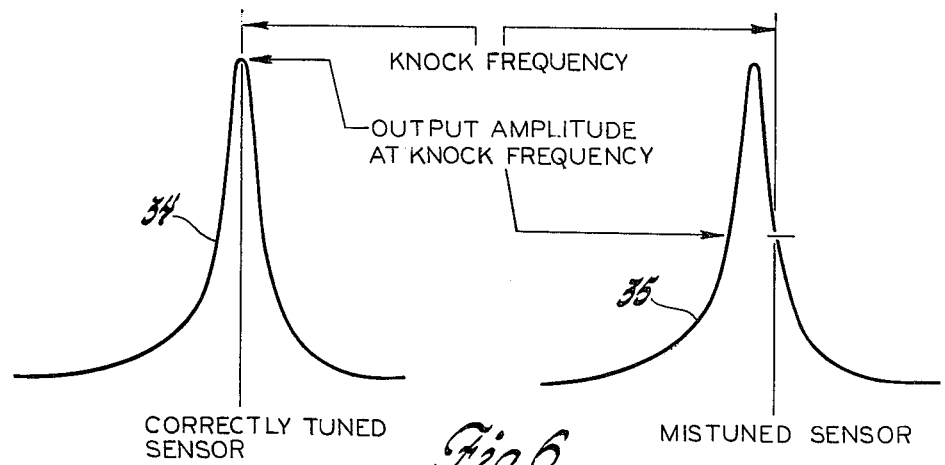
FIG. 6 shows output versus frequency curves for two sensors for use in the apparatus of FIGS. 1-3.

Referring to FIGS. 1 and 6, a prior art method of knock intensity measurement will be described along with one of its major shortcomings. In the system of FIG. 1, the output of vibration sensor 27 is provided to a bandpass filter 30 and a noise reference generator 31. Noise reference generator 31, which may be of the type described at a later point in this description, includes rectifier and low pass filter means to produce a unidirectional voltage signal which generally follows the average rectified voltage from the sensor and is adjusted by suitable amplifier means to be less than the peaks in the sensor signal due to knock induced vibrations but greater than most of the rest of the sensor signal. The outputs of bandpass filter 30 and noise reference generator 31 are provided to a comparator 32, which generates an output only when the output of bandpass filter 30 exceeds the output of noise reference generator 31. The output of comparator 32 thus comprises a knock intensity signal which can be used as it is or further processed in circuitry to be described at a later point in this specification.

It can be seen that, since the noise reference generator 31 receives its input directly from the sensor, its frequency content will not be affected by bandpass filter 30 and it can thus be considered to generate a broadband noise reference signal. Referring to FIG. 6, curve 34 is a frequency response curve of a sensor 27 which is correctly tuned to the characteristic or knock frequency to which bandpass filter 30 is also tuned. Curve 35, on the other hand, is the frequency response curve of a sensor which is tuned to some other frequency slightly different from the characteristic or knock frequency to which bandpass filter 30 is tuned. It can be seen that the central peak of each curves 34 and 35 is approximately equal in height and width and will thus make the same contribution to the average broadband noise level is generated in noise reference generator 31. However, as can be seen in FIG. 6, the signal at the characteristic or knock frequency to which bandpass filter 30 is tuned will be significantly different in amplitude between sensors represented by curves 34 and 35. Thus, comparator 32 will produce a different output knock intensity signal for the two sensors.

Figure 2:
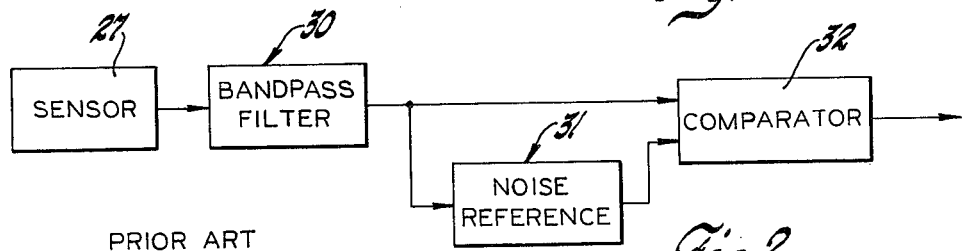
FIG. 2 shows a block diagram of another prior art embodiment of engine knock signal generating apparatus.

FIG. 2 shows a system in which noise reference generator 31 derives its input from the output of bandpass filter 30 rather than from sensor 27 itself. The result is that the noise reference level signal from noise reference generator 31 is no longer a broadband noise reference level but is indicative of the average level at the characteristic or knock frequency to which bandpass filter 30 is tuned. Thus, referring to FIG. 6, if the sensor tuning changed from that represented by curve 34 to that of curve 35, the amplitude of the noise reference level from noise reference generator 31 would be decreased in the same proportion as the amplitude of the signal from bandpass filter 30; and comparator 32 would not be greatly affected by the change.

However, an additional characteristic of the system of FIG. 2 is the magnified contribution of the knock peaks themselves to the average noise level generated by noise reference generator 31. This is to be expected, since such knock-induced peaks at the characteristic or knock frequency are passed by bandpass filter 30 to noise reference generator 31 substantially full strength while signals at other frequencies passed to noise reference generator 31 are substantially attenuated by bandpass filter 30. The result can be seen in the waveforms of FIG. 4, where waveform 37 represents a typical portion of the output of sensor 27 having knock-induced peaks 38 representing the decaying vibrations from a single knock event. Waveform 40 shows the output of bandpass filter 30 while waveform 41 superimposed on waveform 40 shows the output of noise reference generator 31 in the system of FIG. 2. The contribution of the peaks 42 of waveform 40, which peaks occur at the characteristic or knock frequency, on the amplitude of curve 41 are seen to be considerable. In this case, the growth in amplitude of waveform 41 is substantial enough that the last of the peaks 42 does not produce an output signal pulse 44 in the waveform 45, which represents the output of comparator 32 in FIG. 2. Waveform 45 is thus seen to understate the intensity of the knock which produced peaks 38 of waveform 37; and this understatement can be significant in the case of strong or heavy knock. The result in the system of FIG. 8 may be an insufficient spark retard which may allow knock at an objectionable level.

Figure 3:
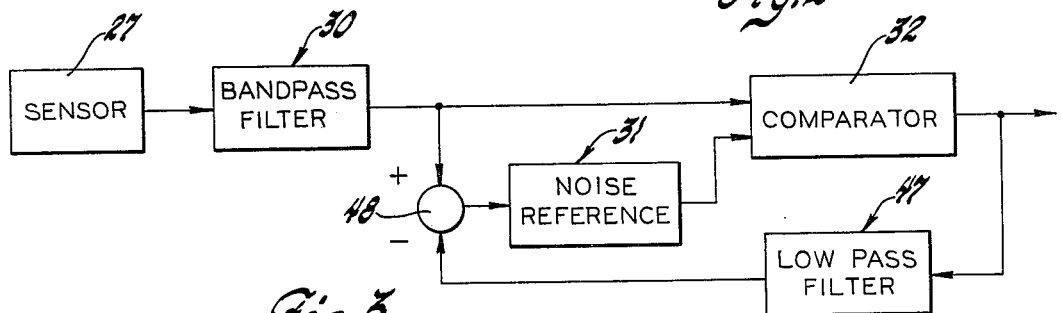
FIG. 3 shows a block diagram of a preferred embodiment of engine knock signal generating apparatus according to this invention.

The system of this invention, as seen in FIG. 3, derives its input to the noise reference generator 31 partly from bandpass filter 30 so that the knock intensity signal of comparator 32 remains valid even if the tuning characteristics of sensor 27 change. However, the input to noise reference generator 31 is also derived from the output of a low pass filter 47 which is subtracted from the output of bandpass filter 30 in a summing junction 48. Low pass filter 47 receives its input from the output of comparator 32 so that low pass filter 47 and summing junction 48 comprise a negative or noise channel inhibiting feedback loop around noise reference generator 31 and comparator 32.

Figure 4:
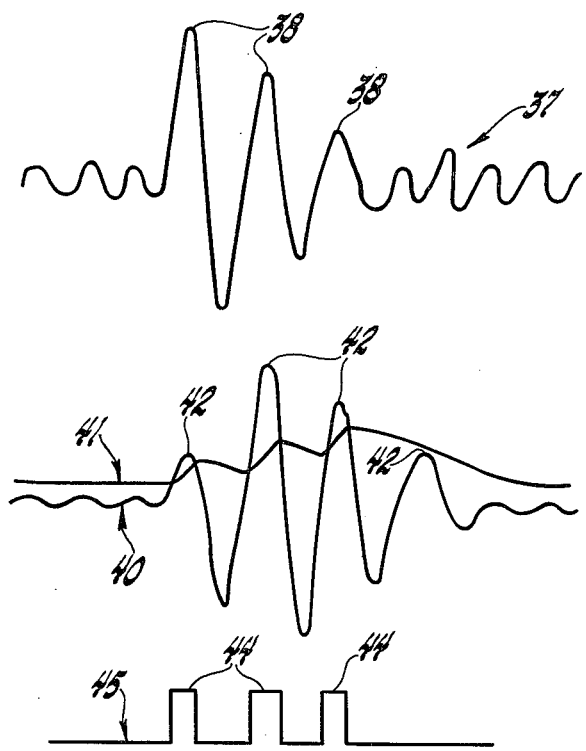
FIG. 4 shows some time-varying waveforms associated with the apparatus of FIG. 2.
Figure 5:
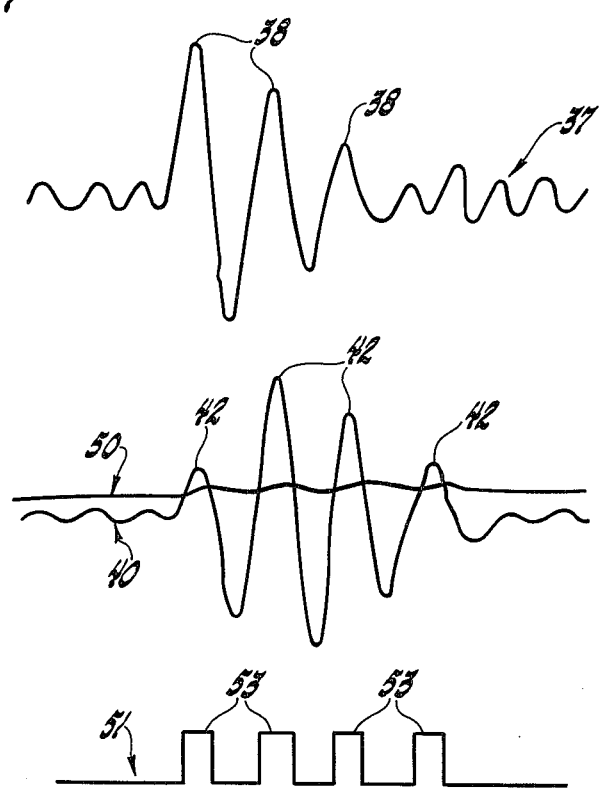
FIG. 5 show some time-varying waveforms associated with the apparatus of FIG. 3.
Figure 5:

Referring to FIG. 5, waveform 37 shows the output of sensor 27 and is identical to waveform 37 of FIG. 4. Waveform 40 shows the output of bandpass filter 30 and is identical to waveform 40 of FIG. 4. However, the output of noise reference generator 31 in FIG. 3 is shown in a waveform 50 superimposed on waveform 40 in FIG. 5. The outputs of comparator 32 and low pass filter 47 in FIG. 3 are shown as waveforms 51 and 52, respectively, in FIG. 5.

It can be seen that the output of low pass filter 47 is essentially zero except when knock pulses 53 appear in the output of comparator 32. Knock pulses 53 cause peaks 54 in the output of low pass filter 47 which tend to reduce the growth of waveform 50 during those times when peaks 42 are present in the output of bandpass filter 30. The result is a more even noise reference level as seen in waveform 50 and a knock intensity signal as seen in waveform 51 which more closely represents the actual knock intensity. A comparison of waveform 51 with waveform 45 shows that, not only are there four knock pulses 53 compared with only three knock pulses 44, but each of the knock pulses 53 is somewhat wider than the corresponding knock pulse 44, since peaks 42 of waveform 40 are intercepted by waveform 50 at a lower and therefore wider point than by waveform 41.

Figure 7:
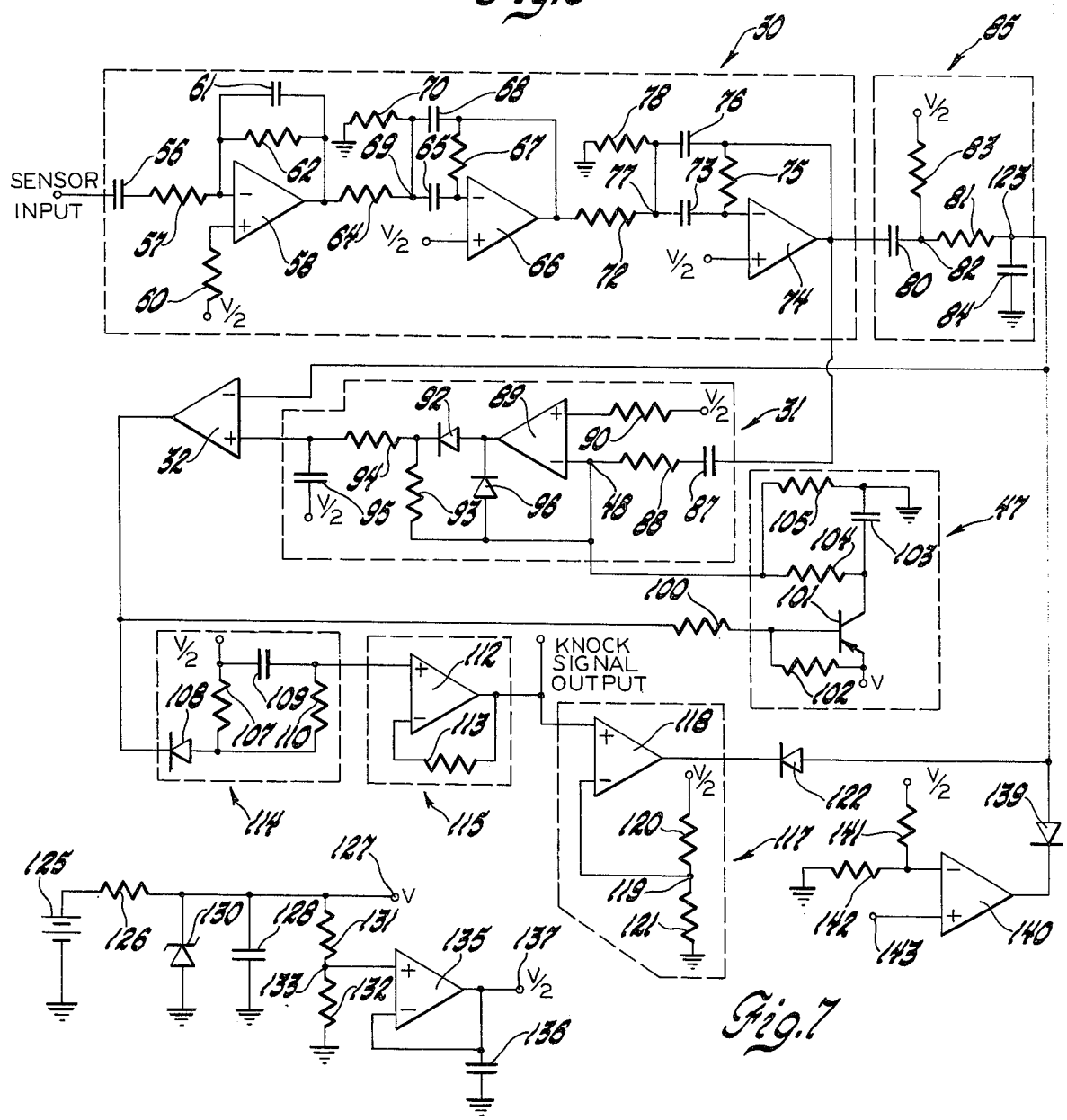
FIG. 7 shows a circuit diagram of a preferred embodiment of the apparatus shown in block diagram form in FIG. 3.

A circuit embodiment of the system shown in FIG. 3 is shown in FIG. 7. Referring to FIG. 7, the output of sensor 27 of FIG. 13 is connected through a capacitor 56 and resistor 57 to the inverting input of an operational amplifier or op-amp 58. The non-inverting input of op-amp 58 is connected through a resistor 60 to a power source V/2, to be further described at a later point in this specification. The output of op-amp 58 is connected back to the inverting input through a capacitor 61 and resistor 62 in parallel and is further connected through a resistor 64 and capacitor 65 in series to the inverting input of an op-amp 66. The non-inverting input of op-amp 66 is connected to power source V/2 and the output is connected through a resistor 67 to the inverting input, through a capacitor 68 to the junction 69 of resistor 64 and capacitor 65, through capacitor 68 and a resistor 70 in series to ground and through a resistor 72 and capacitor 73 in series to the inverting input of an op-amp 74. The non-inverting input of op-amp 74 is connected to power source V/2; and the output is connected through a resistor 75 to the inverting input, through a capacitor 76 to the junction 77 of resistor 72 and capacitor 73 and through capacitor 76 and a resistor 78 in series to ground.

The elements described to this point comprise the bandpass filter 30 and actually consist of three bandpass filters connected in cascade. Op-amp 58 and its associated element comprise a first bandpass filter; while op-amps 66 and 74, along with their associated elements, comprise two identical high Q bandpass filters of the active resonant type. Thus the bandpass filter 30 is seen to be a high Q bandpass filter.

The output of op-amp 74 is connected through a capacitor 80 and resistor 81 in series to the negative input of comparator 32. The junction 82 of capacitor 80 and resistor 81 is connected through a resistor 83 to power source V/2; and the negative input of comparator 32 is connected through a capacitor 84 to ground. Elements 80 through 84 comprise a passive bandpass filter 85 of much lower Q than bandpass filter 30 connecting the output of bandpass filter 30 to one input of comparator 32. This additional filtering means is not required for this invention. Its Q is much lower than that of filter 30 and its main use is reducing the effect of radio frequency interference on comparator 32.

The output of op-amp 74 is also connected through a capacitor 87 and resistor 88 in series to the inverting input of an op-amp 89. The non-inverting input of op-amp 89 is connected through a resistor 90 to power source V/2; and the output of op-amp 89 is connected through a diode 92 and resistor 93 in series to the inverting input, through diode 92 and a resistor 94 to the positive input of comparator 32, and through diode 92, resistor 94 and a capacitor 95 to power source V/2. The inverting input of op-amp 89 is further connected through a diode 96 to the output. Elements 87 through 96 comprise the noise reference generator 31. Diodes 92 and 96 comprise, with op-amp 89 and resistors 90 and 93, a standard half wave rectifier with respect to the voltage level V/2. Resistor 94 and capacitor 95 comprise a low pass filter cascaded with the half wave rectifier to form a standard average detector circuit. The resistors 88 and 93 are selected to provide an appropriate gain to place the output level of noise reference generator 31 below the knock-induced peaks of the signal applied to the negative input of comparator 32 but above the noise in that signal.

The output of comparator 32 is connected through a resistor 100 to the base of a PNP transistor 101, which has an emitter connected to power source V and through a resistor 102 to its base. Transistor 101 further has a collector connected through a capacitor 103 to ground, through a resistor 104 to the inverting input of op-amp 89 and through resistor 104 and a resistor 105 in series to ground. These elements generally comprise the low pass filter 47, which receives an input from comparator 32 through resistor 100 and provides an output to summing junction 48, which comprises the inverting input of op-amp 89.

In the operation of the circuit as described to this point, the input from sensor 27 is filtered by high Q bandpass filter 30, which also references the signal to a reference voltage V/2. The output of bandpass filter 30 below voltage V/2 is passed by diodes 92 and 96, amplified and inverted in op-amp 89, filtered to an average level by capacitor 95 and resistor 94 and applied to one input of comparator 32. The output of filter 85, or substantially the output of filter 30, is applied to the other input of comparator 32; and the output of comparator 32 is at a voltage level V when the filtered sensor signal does not exceed the reference and in output potential of ground when the filtered sensor signal does exceed the noise reference, in the peak of a knock induced engine vibration. Thus, when there are no knock induced engine vibrations, transistor 101 will be turned off, capacitor 103 will discharge to V/2 and there will be no input from low pass filter 47 to summing junction 48. However, when a knock induced engine vibration peak causes an output pulse to be generated by comparator 32, transistor 101 will be turned on by the ground level signal at its base and to charge capacitor 103 and provide an input to summing junction 48 which raises the voltage thereon and thus decreases the output voltage of op-amp 89. The charging of capacitor 103 is very swift to prevent the output of noise reference generator 31 from building up by a quick charge of capacitor 95 through resistor 94. Resistors 104 and 93 establish noise feedback gain. Resistor 105 establishes a fixed DC offset voltage to junction 48 to ensure a high output from op-amp 32 when there is little noise, as at idle.

The remainder of the circuit provides output conditioning for the knock intensity signal of comparator 32 and supplying the required electric power at potential V and V/2. The source of potential V/2 is connected through a resistor 107 and diode 108 to the output of comparator 32. It is further connected through a capacitor 109, and also through resistor 107 and another resistor 110 in series, to the non-inverting input of an op-amp 112, the output of which is connected in feedback through a resistor 113 to its inverting input. Capacitor 109, with diode 108 and resistors 107 and 110 comprise a type of low pass filter or passive integrator 114 with different integration rates in two directions. When a ground level pulse from comparator 32 indicates a knock-induced vibration, capacitor 109 charges at a comparatively fast rate through resistor 110 to drop the voltage input to op-amp 112 from voltage V/2. The fast rate is designed for a particular engine and vehicle to provide quick response to knock but not, if the response is a spark retard, so quick as to result in objectionable surge. Whe the output of comparator 32 is voltage V, however, capacitor 109 discharges through resistors 110 and 107 at a slower rate, for system stability and smooth operation, to raise the voltage input to op-amp 112 slowly toward V/2 again. Op-amp 112 and resistor 113 comprise a buffer 115 to connect the output of integrator 114 to some apparatus to be controlled by the knock intensity signal. The specific circuitry shown herein is specifically designed to be used in the spark timing apparatus described in the aforementioned West patent application Ser. No. 789,801. A voltage output of voltage V/2 indicates no knock correction; and increasing knock correction is required as the voltage decreases from voltage V/2 toward ground.

Limiter means 117, provided optionally to limit the maximum engine spark retard due to the output signal of this invention, comprises an op-amp 118 having its non-inverting input connected to the output of op-amp 112 and its inverting input connected to the junction 119 of a pair of resistors 120 and 121 connected in series between potential V/2 and ground. A diode 122 is connected from the junction 123 of resistor 81 and capacitor 84 in filter 85 to the output of op-amp 118. Limiter 117 in operation has no effect on the output of op-amp 112 until that output decreases to a level determined by the voltage at junction 119. At this point, rather than merely clamping the voltage on the output of op-amp 112, limiter 117 shunts the negative input of comparator 32 to ground to prevent the buildup of any higher voltage on capacitor 109 in integrator 114. Thus, there is no recovery lag when the period of limiting ends while capacitor 109 discharges, as would be the case if the output of op-amp 112 alone were clamped.

The electrical voltage and current for the circuit of FIG. 7 is obtained from the normal vehicle power supply through a circuit to be described below. Battery 125 represents the normal motor vehicle battery or alternator and voltage regulator. It is connected through a resistor 126 to a terminal 127 from which is obtained voltage V. A capacitor 128 and zener diode 130 are connected in parallel across terminal 127 and ground for additional regulation. A pair of resistors 131 and 132 of identical, accurately determined resistance are connected in series across terminal 127 and ground to form a voltage divider at their junction 133, which is connected to the non-inverting input of an op-amp 135. The output of op-amp 135 is connected to the inverting input in feedback and through a capacitor 136 to ground, and further provides a terminal 137 from which is obtained voltage V/2. The applications of voltages V and V/2 are as indicated in the circuit of FIG. 7; and, in addition, whatever other electrical connections are necessary, such as the appropriate power connections to the op-amps, are obtained from terminal 127 and vehicle ground.

Typical values of the circuit elements in FIG. 7 are as follows:

| Op-amps and Comparators |
| --- |
| 32, 58, 66, 74, 89, 112, 118 - Motorola MC 1458 |
| 135, 140 - National Semiconductor LM 2904 |

| Diodes |
| --- |
| 92, 96, 108, 122, 139 - 1N485B |
| 130 - 1N4740 |

| Transistors |
| --- |
| 101 - 2N3906 |

| Capacitors |
| --- |
| 56 - 390 pF |
| 61 - 22 pF |
| 65, 68, 73, 76, 80, 87, 103 - .01 mF |
| 84 - 150 pF |
| 95 - 2.7 mF |
| 109 - 4.7 mF |
| 128 - 39 mF |
| 136 - 22 mF |

| Resistors | |
| --- | --- |
| 57 - 75 K | 102 - 5.1 K |
| 60, 62, 107, 113 - 1 M | 104 - 20 K |
| 64, 72 - 12.7 K, 1% | 105 - 5.1 M |
| 67, 75 - 25.5 K, 1% | 110 - 1K |
| 70, 78 - 261 ohm, 1% | 120 - 9.76 K |
| 81 - 100 K | 121 - 37.4 K |
| 83, 88 - 10 K | 126 - 150 ohm, ½ w |
| 90, 93 - 68 K | 131, 132 - 10.0 K, 1% |
| 94 - 51 K | 141 - 499 K, 1% |
| 100 - 47 K | 142 - 402 K, 1% |

An optional circuit comprising an op-amp 140 having an inverting input supplied with a reference voltage from a voltage divider comprising resistors 141 and 142 across voltage V/2 and an output connected through a diode 139 from junction 123 is effective to shunt that junction to ground when an engine speed voltage applied to non-inverting input 143 of op-amp 140 indicates that engine speed is lower than a predetermined reference. This circuit may be included if it is desired to cut out retard below a predetermined speed, which might be set a few hundred RPM above idle, to ensure full acceleration from engine idle.

The embodiment described above is a preferred embodiment of this invention; however, equivalent embodiments within the scope of the claims will occur to those skilled in the art. Therefore, this invention should be limited only by the claims which follow.

The embodiments of the invention in which an exclusive property or privilege is claimed are defined as follows:

1. Apparatus for use with an internal combustion engine having ringing knock-induced vibrations at a characteristic frequency and other vibrations, the apparatus being effective to generate knock signals representing the knock level therein and comprising, in combination:
    a vibration sensor mounted on said engine and responsive to both said ringing knock-induced vibrations and said other vibrations to generate a signal;
    a bandpass filter having maximum transmission at said characteristic frequency and responsive to the signal from said sensor during a knock-induced ringing vibration to generate a filtered sensor signal having attenuated components at frequencies other than the characteristic frequency compared with those at the characteristic frequency;
    average detector means responsive to said bandpass filter for generating from the filtered sensor signal a unidirectional noise reference signal generally proportional to the average unidirectional amplitude of the filtered sensor signal at a higher amplitude than all but the peaks of those components due to knock-induced engine vibrations;
    a comparator effective to compare the filtered sensor signal to the unidirectional noise reference signal and to generate knock signals when the filtered sensor output signal exceeds the unidirectional DC noise reference;
    low-pass filter means responsive to said knock signals to generate a unidirectional noise reference inhibit signal therefrom;
    feedback means connected to apply said unidirectional noise reference inhibit signal to said unidirectional DC noise reference signal generating means in sense to limit the unidirectional noise reference signal when knock signals are generated, whereby the tendency of components due to knock-induced vibrations in the filtered sensor signal to falsely increase the unidirectional noise reference is reduced and the knock signals more accurately represent the level of knock in said engine.

2. The method of detecting knock in an internal combustion engine having ringing, knock-induced vibrations at a characteristic frequency and other vibrations and generating knock signals representing the intensity of such knock, comprising the steps:
    sensing the knock-induced and other vibrations and generating a time-varying signal in response thereto;
    attenuating components of the time-varying signal not of the characteristic frequency with respect to components at the characteristic frequency to form a filtered time-varying signal;
    detecting, averaging and amplifying the filtered time-varying signal to form a unidirectional noise reference signal generally proportional to the average unidirectional amplitude of the filtered time-varying signal at an amplitude higher than all but the peaks of those components due to knock-induced engine vibrations;
    comparing the filtered time-varying signal to the unidirectional noise reference signal and generating knock signals when the former exceeds the latter;
    low pass filtering the knock signals to form a unidirectional noise reference inhibit signal;
    reducing the amplitude of the unidirectional noise reference signal by a proportion of the unidirectional noise reference inhibit signal in feedback to limit the unidirectional noise reference signal when knock signals are generated, whereby the tendency of the unidirectional noise reference signal to rise due to knock-induced vibration components of the filtered time-varying signal is reduced and the knock signals more accurately represent the intensity of knock in the engine.

* * * * *